United States Patent [19]
Pehu et al.

[11] Patent Number: 5,922,649
[45] Date of Patent: Jul. 13, 1999

[54] IMPROVING THE YIELD OF PLANTS

[75] Inventors: Eija Pehu, Helsinki; Jussi Hautala, Turku; Esko Kokkonen, Espoo, all of Finland

[73] Assignee: Cultor OY, Finland

[21] Appl. No.: 08/793,282

[22] PCT Filed: Sep. 7, 1995

[86] PCT No.: PCT/FI95/00481

§ 371 Date: Apr. 10, 1997

§ 102(e) Date: Apr. 10, 1997

[87] PCT Pub. No.: WO96/41530

PCT Pub. Date: Dec. 27, 1996

[30] Foreign Application Priority Data

Jun. 9, 1995 [FI] Finland ..................................... 952865

[51] Int. Cl.$^6$ .......................... A01N 37/00; A01N 37/02; A01N 37/30
[52] U.S. Cl. ........................... 504/320; 504/345; 514/556
[58] Field of Search ............................. 47/48.5, DIG. 10; 800/200; 504/320, 345; 514/556

[56] References Cited

FOREIGN PATENT DOCUMENTS 0 181 494   5/1986   European Pat. Off. .
WO 9535022   12/1995   WIPO .

OTHER PUBLICATIONS

STN International, File WPIDS, WPIDS, accession. No. 89–312201, Chikkarin K: "Pant supported on basal be—is cultivated with nourishing liq. Contg. Betaine (s)"; & JP, A, 01228416, 890912(8943) Sep. 1989.

Journal of Experimental Botany, vol. 38, No 188, Mar. 1987, M.I. Lone et al, "Influence of Proline and Glycinebetaine on Salt Tolerance of Cultured Barley Embryos" p. 479–p. 490.

Plant Science Letters, vol. 25, 1982, C. Itai et al, "Responses of Water–Stressed Hordeum Distichum L. And Cucmis Sativus to Proline and Betaine" p. 219–p. 335.

J. Plant Physiol., vol. 140, 1992, Y Zhao et al, "Protecton of Membrane Integrity in Medicago sativa L. By Glycinegetaine against the Effects of Freezing" p. 541–p. 543.

Patent Abstracts of Japan, vol. 13, No. 516, C–656, abstract of JP, A, 1–208386 (Katakura Chitsukarin K.K.), Aug. 22, 1989 (22.08.89).

Ed. L. Chester, in Adjuvants for Agrichemicals , CRC Press, Boca Raton , FL.. pp. 17–20 , 595–599 , 691, 1992.

Aberg Swedish J. Agric. Res. 12:51–61, 1982 "Plant Growth Regulators".

*Primary Examiner*—Allen J. Robinson
*Attorney, Agent, or Firm*—Nixon & Vanderhye

[57] ABSTRACT

Exogenous use of betaine and adjuvant improves the yield of plants. Betaine and adjuvant can be applied either together or separately and used under both normal and stress conditions. Also disclosed are combinations of betaine and adjuvant, treatment of plants exogenously with betaine and adjuvant, and products obtained from such plants.

6 Claims, No Drawings

IMPROVING THE YIELD OF PLANTS

This application is a 371 of PCT/FI95/00481, filed Sep. 7, 1995.

TECHNICAL FIELD

The invention relates to the use of betaine to improve the yield of plants. The invention relates especially to the combined use of betaine and adjuvant to improve the yield of plants. According to the invention, the yield can be improved both under normal and stress conditions, i.e. when the conditions are poor due to e.g. low temperatures, drought, high salinity or environmental poisons interfering with the growth. The invention also relates to a combination of betaine and adjuvant, to plants treated with betaine and adjuvant, and to products obtained from such plants.

BACKGROUND

The environment and conditions of growth considerably affect the yield of plants. Optimum growth environment and conditions usually result in a yield that is large in quantity and high in quality. Under poor growth conditions both the quality and the quantity naturally deteriorate.

The physiological properties of a plant are preferably manipulated by means of breeding, both with traditional breeding methods and for example with genetic manipulation.

Several different solutions concerning cultivation technique have been developed to improve the growth conditions and yield of plants. Selecting the right plant for the right growth location is self-evident for a person skilled in the art. During the growing season plants may be protected with mechanical means by utilizing for example different gauzes or plastics or by cultivating the plants in greenhouses. Irrigation and fertilizers are generally used in order to improve the growth. Surfactants are often used in connection with applying pesticides, protective agents and minerals. Surfactants improve the penetration of substances to plant cells, thereby enhancing and increasing the effect of the aforementioned agents and simultaneously reducing their harmful effects on the environment. However, different methods of cultivation technique are often laborious and impractical, their effect is limited (the economical size of a greenhouse, the limited protection provided by gauzes, etc.), and they are also far too expensive on a global scale. No economically acceptable chemical solutions for protecting plants from environmental stress conditions have been described so far.

Water supply is more important than any other environmental factor for the productivity of a crop, even though the sensitivity of plants to drought varies. Irrigation is usually utilized to ensure sufficient water supply. However, there are significant health and environmental problems related to irrigation, for example a sharp decrease in water resources, deterioration of water quality and deterioration of agricultural lands. It has been calculated in the field that about half of the artificially irrigated lands of the world are damaged by waterlogging and salinization. An indication of the significance and scope of the problem is that there are 255 million hectares of irrigated land in the world, and they account for 70% of the total world water consumption. In the United States alone, there are over 20 million hectares of irrigated land mainly in the area of the 18 western states and in the southeastern part of the country. They use 83% of the total water consumption for irrigation alone. It can also be noted that the use of irrigation water increases every year especially in industrial countries. In addition to these problems, another drawback of irrigation is the high cost.

Another serious stress factor is the salinity of soil. The salinity of soil can be defined in different ways; according to the general definition, soil is saline if it contains soluble salts in an amount sufficient to interfere with the growth and yield of several cultivated plant species. The most common of the salts is sodium chloride, but other salts also occur in varying combinations depending on the origin of the saline water and on the solubility of the salts.

It is difficult for plants growing in saline soil to obtain a sufficient amount of water from the soil having a negative osmotic potential. High concentrations of sodium and chloride ions are poisonous to plants. An additional problem is the lack of minerals, which occurs when sodium ions compete with potassium ions required, however, for cell growth, osmoregulation and pH stabilization. This problem occurs especially when the calcium ion concentration is low.

The productivity of plants and their sensitivity to the salinity of soil also depend on the plant species. Halophytes require relatively high sodium chloride contents to ensure optimum growth, whereas glycophytes have low salt tolerance or their growth is considerably inhibited already at low salt concentrations. There are great differences even between different cultivars of a cultivated plant species. The salt tolerance of one and the same species or cultivar may also vary depending for example on the stage of growth. In the case of low or moderate salinity, the slower growth of glycophytes cannot be detected in the form of specific symptoms, such as chlorosis, but it is shown in the stunted growth of the plants and in the colour of their leaves that is darker than normal. Moreover, the total leaf area is reduced, carbon dioxide assimilation decreases and protein synthesis is inhibited.

Plants can adapt to some extent to stress conditions. This ability varies considerably depending on the plant species. As a result of the aforementioned stress conditions, certain plants begin to produce a growth hormone called abscisic acid (ABA), which helps the plants to close their stomata, thus reducing the severity of stress. However, ABA also has harmful side effects on the productivity of plants. ABA causes for example leaf, flower and young fruit drop and inhibits the formation of new leaves, which naturally leads to reduction in yield.

Stress conditions and especially lack of water have also been found to lead to a sharp decrease in the activity of certain enzymes, such as nitrate reductase and phenylalanine ammonium lyase. On the other hand, the activity of alpha-amylase and ribonuclease increases. No chemical solutions, based on these findings, to protect plants have been described so far.

It has also been found that under stress conditions certain nitrogen compounds and amino acids, such as proline and betaine, are accumulated in the regions of growth of certain plants. The literature of the art discusses the function and meaning of these accumulated products. On the one hand it has been proposed that the products are by-products of stress and thus harmful to the cells, on the other hand it has been estimated that they may protect the cells (Wyn Jones, R. G. and Storey, R.: *The Physiology and Biochemistry of Drought Resistance in Plants*, Paleg, L. G. and Aspinall, D. (Eds.), Academic Press, Sydney, Australia, 1981).

Zhao et al. (in J. Plant Physiol. 140 (1992) 541–543) describe the effect of betaine on the cell membranes of alfalfa. Alfalfa seedlings were sprayed with 0.2M glycinebetaine, whereafter the seedlings were uprooted from the substrate, washed free of soil and exposed to temperatures from −10° C. to −20° C. for one hour. The seedlings were then thawed and planted in moist sand for one week at which time regrowth was apparent on those plants that had survived. Glycinebetaine clearly improved the cold stability of alfalfa. The effect was particularly apparent at −6° C. for the cold treatment. All controls held at −6° C. for one hour died, whereas 67% of the seedlings treated with glycinebetaine survived.

Itai and Paleg (in *Plant Science Letters* 25 (1982) 329–335) describe the effect of proline and betaine on the recovery of water-stressed barley and cucumber. The plants were grown in washed sand, and polyethylene glycol (PEG, 4000 mol. wt.) was added to the nutrient solution for four days in order to produce water stress, whereafter the plants were allowed to recover for four days before harvesting. Proline and/or betaine (25 mM, pH 6.2) was sprayed on the leaves of the plant either on the first or third day of the stress or immediately before harvesting. As regards barley, it was noted that betaine supplied either before or after the stress had no effect, whereas betaine added in the end of the stress was effective. Proline had no effect. No positive effect was apparent for cucumber. On the contrary, it was found out that both betaine and proline had a negative effect.

Experiments aiming at clarifying the effects of betaine and proline on plants have thus yielded contradictory results. There are no commercial applications based on these results. The literature of the field does not describe a combination of betaine and adjuvant or the combined use of betaine and adjuvant.

BRIEF DESCRIPTION OF THE INVENTION

The purpose of the present invention was to find a way to partially replace artificial irrigation so that the amount and quality of the yield could be simultaneously ensured. Another purpose of the invention was to find a way to protect plants also under other stress conditions, such as during high salinity often connected with drought, at low temperatures, etc. Moreover, a further aim was to find a way to increase the yield under normal conditions without utilizing methods that would consume environmental resources or harm the environment.

In connection with the present invention it has now surprisingly been found that the yield of plants can be considerably improved by means of betaine and adjuvant that are applied exogenously. Betaine has been found to be effective in improving the yield both under normal and stress conditions, and it has no such detrimental effects as the side effects of ABA. The adjuvant improves the betaine absorption of plant cells acting thus synergistically with betaine. The invention makes it possible to considerably reduce for example the need for artificial irrigation, thus saving the environment and cutting down the costs to a great extent.

The invention thus relates to the exogenous use of betaine and adjuvant to improve the yield of plants. According to the invention, betaine and adjuvant are used exogenously to improve the yield of plants under both normal and stress conditions.

The invention also relates to a method for improving the yield of plants, in which method betaine and adjuvant are exogenously applied to growing plants.

The invention also relates to a combination of betaine and adjuvant that can be utilized exogenously to improve the yield of plants.

The invention also relates to plants treated exogenously with betaine and adjuvant, to products prepared of the plants, and to their use as such and as raw material for food industry.

Betaine and adjuvant are applied to a plant in either one or several successive treatments. Betaine and adjuvant can be used as a combination or applied to the plant separately but more or less simultaneously. If desired, betaine and adjuvant can be used together with conventional fertilizers or pesticides, etc. The application may be performed for example by spraying, and the agents can then be sprayed simultaneously or separately. According to the purposes of the invention, the adjuvant improves the transportation of betaine to plant cells, where betaine actively regulates the osmotic balance of the cells and also participates in other processes of cell metabolism. A cell treated with betaine is more viable even when subjected to exogenous stress factors.

The betaine and adjuvant treatment according to the invention is economically advantageous, and the yield increases in an amount that is economically profitable and significant. The treatment does not produce significantly more work since it may be performed together with conventional sprayings of fertilizers or pesticides, and it does not require new investments in machinery, equipment or space. It must also be noted that betaine is a non-toxic natural product, which has no detrimental effects on the quality of the yield. Betaine is also a stable substance that remains in the plant cells and thereby has a long-standing effect.

DETAILED DESCRIPTION OF THE INVENTION

Betaine refers to fully N-methylated amino acids. Betaines are natural products that have an important function in the metabolism of both plants and animals. One of the most common betaines is a glycine derivative wherein three methyl groups are attached to the nitrogen atom of the glycine molecule. This betaine compound is usually called betaine, glycinebetaine or trimethylglycine, and its structural formula is presented below:

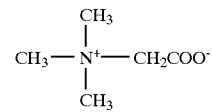

Other betaines are for example alaninebetaine and prolinebetaine, which has been reported to for example prevent perosis in chicks. R. G. Wyn Jones and R. Storey describe betaines in detail in *The Physiology and Biochemistry of Drought Resistance in Plants* (Paleg, L. G. and Aspinall, D. (Eds.), Academic Press, Sydney, Australia, 1981). The publication is included herein by reference.

Betaine has a bipolar structure and it contains several chemically reactive methyl groups which it can donate in enzyme-catalyzed reactions. Most organisms can synthesize small amounts of betaine for example for the methyl function, but they cannot react to stress by substantially increasing the production and storage of betaine. Best known organisms accumulating betaine are plants belonging to the Chenopodiaceae family, for example sugar beet, and some microbes and marine invertebrates. The main reason for the betaine accumulation in these organisms is probably that betaine acts as an osmolyte and thus protects the cells from the effects of osmotic stress. One of the main functions of betaine in these plants and microbes is to increase the osmotic strength of the cells when the conditions require this, for example in case of high salinity or drought, thus preventing water loss. Unlike many salts, betaine is highly compatible with enzymes, and the betaine content in cells and cell organelles may therefore be high without having any detrimental effect on the metabolism. Betaine has also been found to have a stabilizing effect on the operation of macromolecules; it improves the heat resistance and ionic tolerance of enzymes and cell membranes.

Betaine can be recovered for example from sugar beet with chromatographic methods. Betaine is commercially available from Cultor Oy, Finnsugar Bioproducts as a product that is crystalline water-free betaine. Other betaine products, such as betaine monohydrate, betaine hydrochloride and raw betaine liquids, are also commercially available and they can be used for the purposes of the present invention.

According to the present invention, betaine is used exogenously with adjuvant to improve the yield of plants. According to the invention, betaine and adjuvant are used exogenously to improve the yield of plants under both normal and stress conditions. Betaine has thus been found to be useful also when plants are cultivated under stress conditions, i.e. when the plants are subjected to periodic or continuous exogenous stress. Such exogenous stress factors include for example drought, humidity, low or high temperatures, high salinity, herbicides, environmental poisons, etc. Treating plants subjected to stress conditions exogenously with betaine for example improves the adaptation of the plants to the conditions and maintains their growth potential longer, thereby improving the yield-producing capacity of the plants.

Even though this reference and the claims use the words 'betaine' and 'adjuvant', it is clear that according to the invention several different betaines and/or adjuvants can be used, if desired. It should also be noted that betaine is used here as a general term which thus covers different known betaines.

The treatment according to the invention, i.e. the exogenous application of betaine and adjuvant, can improve the yield of both plants that do not normally store betaine in their cells, and plants that even normally can store betaine in their cells. Betaine is a stable substance that remains in the plant cells. The positive effect of betaine is thereby long-standing and diminishes only gradually due to dilution caused by the growth.

The function of the adjuvant is to improve the betaine absorption of plant cells, thus ensuring, improving and enhancing the positive effects of betaine on plants. Any adjuvant known in the art can be used as adjuvant. Adjuvants are described e.g. in *Adjuvants in Crop Protection* (DS 86), PJB Publications Ltd, November 1993, which is included herein by reference. There are several commercially available products that are structurally different and have different effects and differing quality. In addition to these, it is possible to form compositions with similar effect by mixing desired components before use. Adjuvants useful for the purposes of the invention thus include, but are not limited to, e.g. activating additives, such as agents affecting the absorption. These include for example agents based on emulsifiable oils, such as the commercial products Jurttiöljy 33E (imported to Finland by Sareko Agri Oy, Turku, Finland), Kemiroil (Kemira Agro Oy), Sunoco (Sun Oil Company) and Agrirob (Robbe SA., France), and phospholipid- and lecithin-based agents, such as LI-700 (Loveland Industries Inc., Greeley, Colo., USA). Another large group is formed by additives affecting the working solution, such as the spray solution, and they include both the actual surfactants and fixing agents. Surfactants are further divided into cationic, such as the commercial product Exell (Siegfried Agro, Zofingen, Switzerland) and non-ionic, like Sito+ (Witco AS), Activator 90 (Loveland Industries Inc., Colo., USA), Citowett (BASF), and Agral (Zeneca Agro). Fixing agents include for example synthetic latexes, such as BOND (Loveland Industries Inc., Colo., USA). Other examples are given for example in the aforementioned reference *Adjuvants in Crop Protection*.

The aforementioned examples disclose that several different types of adjuvants can be used with betaine for the purposes of the invention. The selection of the adjuvant may also depend on both the plant variety and the conditions of growth. Activating agents containing phospholipid and especially lecithin, such as LI-700, and non-ionic surfactants, like Sito+, have been found to be advantageous within the scope for this invention. The most preferable adjuvant to be used according to the present invention together with betaine to improve the yield of plants is a combination of soy lecithin and carboxylic acid, supplied for example under the trademarks LI-700 (Loveland Industries Inc., Greeley, Colo., USA) and SPRAYMATE LI-700 (Newman Agrochemicals Limited, Barton, Cambridge, England). LI-700 is a penetrating and wetting agent which, according to the manufacturer, improves especially the penetration of systemic fungicides, herbicides and insecticides, as well as micronutrients, such as organic and chelated manganese, copper and iron, into cells. LI-700 is a liquid water-based composition, which mainly contains soy lecithin and propionic acid. According to the manufacturer, a normal amount to be used is about 0.4 to 0.5% of the preparation used for treating plants. Sito+ (Witco AS) is a liquid non-ionic fixing agent that contains ethoxylated alcohol as the active ingredient.

According to the invention, the agents are applied to plants in either one or several successive treatments. The amounts used vary depending for example on the plant species, the cultivar and the phase of growth. For example in the case of potato, about 0.1 to 20 kg of betaine can be used per hectare. A useful amount is thus for example about 10 kg of betaine per hectare, which corresponds to about 0.01% of the potato biomass. A preferable amount is about 2 to 8 kg of betaine per hectare. For tomato, about 0.1 to 30 kg of betaine per hectare can be used. A preferable amount is about 1 to 6 kg/ha. The useful amount of the adjuvant varies greatly depending on the quality of the agent, but it can be for example about 0.05 to 5.0 l/ha, preferably 0.2 to 2.0 l/ha. According to the invention, a combination of betaine and adjuvant is preferably used, in particular an aqueous solution containing about 0.01 to 0.5 M, preferably 0.05 to 0.3M, of betaine and about 0.01 to 1%, preferably 0.1 to 0.5%, of adjuvant calculated from the volume of the solution. The amounts given here are only suggestive; the scope of the present invention thus contains all amounts that work in the manner described herein.

Any method suitable for the purpose can be utilized for applying betaine and adjuvant. Betaine and adjuvant can easily be applied for example through spraying. Such spraying can be performed together with some usual spraying of fertilizers or pesticides, if desired. According to the invention, betaine and adjuvant can be used either separately or in combination. An aqueous solution of betaine and adjuvant is preferably used.

The time of the treatment according to the invention may vary, and a suitable time is determined preferably separately for each plant. If the agents are applied in a single treatment, the treatment is usually performed at an early stage of growth, for example on plants of about 5 to 20 cm. If they are applied in two successive treatments, the second spraying is performed preferably in the beginning of flowering or when stress can be forecasted on the basis of the weather.

The treatment according to the invention considerably improves the yield of plants, for example the amount and quality of the yield. The treatment according to the invention is economically advantageous and the increase in the yield is economically profitable and significant. For example the amount of potato yield has been increased by more than 30%, and for tomato the amount of yield has been as much as doubled with a suitable application rate of betaine and adjuvant. It must also be noted that a cell treated according to the invention remains viable even when subjected to exogenous stress factors, such as low temperatures, drought, high salinity, or the like.

The invention will be described in greater detail by means of the following examples. Examples 1 to 4 describe the positive effect of betaine and adjuvant on the yield of different plants, and Examples 5 to 8 describe the positive effect of adjuvants on the betaine uptake of cells. The synergistic effect of betaine and adjuvant is apparent from all the examples. The examples are only provided to illustrate the invention, and they should not be considered to limit the scope of the invention in any way.

EXAMPLE 1

Potato is a plant belonging to the Solanum family, and it does not naturally store betaine in its cells. The effect of betaine and adjuvant on the potato yield was determined under field conditions in two different locations and utilizing four different betaine concentrations: 0 (control), 1.25, 5.0 and 10 kg of betaine per hectare. For the purpose of dosage, an aqueous solution was prepared, the solution containing 2 ml/l of surfactant, Plus-50 (Ciba Geigy), in addition to the desired betaine concentration. The solution was added in an amount of 640 l/ha at 75% ground cover, and a second application was made during the tuber growing stage. The potato cultivar was Russet Burbank. The places of growth varied for climate, in one (1) the climate was warmer and drier than in the other (2) where frost occurred during the growing season. After the harvesting the tubers were graded into unmarketable (small, green and odd-shaped tubers) and marketable ones, and the weight and number of tubers in the categories were determined. The specific gravity of the tubers was determined with the weight in air-weight in water method. Statistical analysis of the results was performed by means of variance analysis utilizing Genstat statistical package.

In location (1), tuber yield per plant increased from a control value of 1.96 kg to 2.42 kg when betaine was used in an amount of 2.5 kg/ha. This was an increase of 23.5% over the control, i.e. about 17 t/ha. The results are shown in Table 1.

TABLE 1

Effect of a combination of betaine and adjuvant on potato yield

| betaine (kg/ha) | Plus-50 (2.56 l/ha) | increase in yield (% of the control) |
|---|---|---|
| 0 | | 100 |
| 1.25 | | 112 |
| 2.50 | | 123.5 |
| 5.00 | | 117.5 |
| 10.00 | | 112.5 |

In location (2), the results deviated to some extent from the results obtained in location (1); an increase of more than 10% in the amount of yield over the control was obtained only at the betaine application rates of 5 and 10 kg/ha. The best result was obtained with the application rate of 10 kg/ha, the yield thus increasing 12.6% over the control, i.e. 7.9 t/ha. With the betaine application rate of 10 kg/ha, a clear increase was also detected in the number of marketable tubers per plant. No significant differences were found in the specific gravity of tubers. The values varied between 1.084 and 1.082.

A clear increase in the yield was apparent in both locations in response to exogenous application of betaine and adjuvant. However, the yield increase was clearly different in the two locations. The differences may result from two different factors. On the one hand, the stress was different in the locations due to differences in the climate. On the other hand, in location (1) the potato tubers were harvested within one week of the second application, and the second application may not have had any influence on the yield. In location (2) betaine and adjuvant were added during the tuber development stage, and the harvesting was performed at maturity about 6 weeks after the application.

EXAMPLE 2

This experiment examined whether the exogenous application of betaine and adjuvant according to the invention can be used to protect plants from damage caused by herbicides. The experimental plant was potato, and the cultivar was Russet Burbank. The experiment was conducted under field conditions, and metribuzin and cyanazine (Bladex) were used as herbicides and added at a late stage of growing. Five different concentrations of betaine were used: 0 (control), 2, 4, 8 and 12 kg of betaine per hectare. For the purpose of dosage, an aqueous solution was prepared, and in addition to the desired betaine concentration the solution contained 1 ml/l of surfactant, Plus-50 (Ciba Geigy). The solution was added in an amount of 640 l/ha at 25% ground cover. The place of growth situated at an altitude of 140 m and was periodically plagued by high temperatures and drought. The crop was harvested manually, and the tubers were graded into unmarketable (small, green and diseased tubers) and marketable ones, and the weight and number of tubers in the categories were determined.

In this experiment too, the treatment according to the invention increased the number of tubers. The smallest betaine application rates, 2 to 4 kg/ha, had no significant effect on the yield and the number of tubers. With the highest betaine contents the yield and the number of tubers were significantly increased. The number of tubers per hectare increased the most with the betaine content of 8 kg/ha, the increase thus being 21% over the control. The results are shown in Table 2.

TABLE 2

Effect of a combination of betaine and adjuvant on the yield of potato treated with a herbicide

| | | number of tubers | |
|---|---|---|---|
| Betaine (kg/ha) | Plus-50 (0.64 l/ha) | per hectare × $10^3$ | % of the control |
| 0 | | 170 | 100 |
| 2 | | 160 | 94 |
| 4 | | 176 | 103 |
| 8 | | 206 | 121 |
| 12 | | 181 | 106 |

EXAMPLE 3

The effect of betaine and adjuvant on grapevine yield was determined under field conditions utilizing four different betaine concentrations: 0 (control), 1, 2 and 4 kg of betaine per hectare. An aqueous solution was used in the experiment, the betaine concentration of the solution being 12 g/l. The solution also contained 2 ml/l of surfactant, Plus-50 (Ciba Geigy). The amount of solution applied was about 350 l/ha or 64 l/1000 m of a cultivated row, and the application was performed always on each side of the row in order to ensure that the plants were uniformly treated with betaine. The grapevines were otherwise cultivated in a normal manner without irrigation, and they were periodically plagued by drought and cold weather; the temperature varied between about 3 and 30° C. The grapevine cultivar was Pinot Noir. Four uniform-looking vines were selected during budburst. When there was about 50% budburst, but before any flower opening, two of the plants were treated with a single dose of betaine and adjuvant of a certain concentration, whereas the other two vines received at this stage only half of the selected betaine and adjuvant concentrations and the remaining dose was applied a month later in the beginning of flowering. A single application found to be more effective than several applications. When the grapes were ripe, the bunches were picked and the yield was calculated by converting the number of grapes produced by two vines into a yield per hectare on the basis of the number of vines growing within one hectare. The number of bunches per vine was calculated by dividing the total number of bunches of two vines by two. The experiment showed that a single betaine dosage of 2 kg/ha or 4 kg/ha provided a considerably greater yield. The best result was obtained with the betaine dosage of 4 kg/ha, whereupon the yield increased from a control value of 6.5 t/ha to 9.8 t/ha. This signifies a net increase of 3.3 t/ha, i.e. the yield increase was about 51% over the control. The number of grape bunches also increased significantly when betaine was applied in an amount of 2 kg/ha or more. In this case too, the best result was obtained with a betaine application rate of 4 kg/ha. The results are shown in Table 3.

TABLE 3

Effect of a combination of betaine and adjuvant on grapevine yield

| betaine (kg/ha) | Plus-50 (0.7 l/ha) | number of grapes (t/ha) | number of bunches of plant |
|---|---|---|---|
| 0 | | 6.5 | 28.4 |
| 1 | | 7.1 | 31.8 |
| 2 | | 9.1 | 36.2 |
| 4 | | 9.8 | 37.0 |

EXAMPLE 4

The effects of the treatment according to the invention on the quality of grapes were examined by estimating the weight of bunches, the weight of 100 grapes, and the pH and Brix of grape juice of vines cultivated under the circumstances described in Example 3. The weight of the bunches was calculated by dividing the total yield of two vines by the number of bunches, and the weight of 100 grapes was calculated by dividing by two the weight of 200 grapes picked at random. Brix is the measure of the solute content of grape juice, and most of this content is sugar. There were no statistically significant changes in the weight of bunches and the weight of 100 grapes as a result of the treatment according to the invention. There were no statistically significant changes in the pH and Brix of grape juice as a result of the treatment, either. On the basis of the results, the treatment according to the invention did not have a negative effect on the quality of the grapes despite the considerable increase in the yield. Some of the results are shown in Table 4.

TABLE 4

Effect of a combination of betaine and adjuvant on the pH and Brix of grape juice

| Betaine (kg/ha) | Plus-50 (0,7 l/ha) | pH 1. | pH 2. | Brix 1. | Brix 2. |
|---|---|---|---|---|---|
| 0 | | 3.48 | 3.49 | 17.3 | 17.9 |
| 1 | | 3.51 | 3.49 | 17.2 | 17.6 |
| 2 | | 3.46 | 3.52 | 16.4 | 17.8 |
| 4 | | 3.50 | 3.56 | 17.9 | 18.1 |

1. Application in a single treatment.
2. Application in two successive treatments.

EXAMPLE 5

The experiment examined the effect of betaine and adjuvant on wheat, which also accumulates betaine in its cells in nature. The experiments were conducted in greenhouses and the wheat cultivar was Tjalve. Thirty wheat seeds were sown in 7.5 litre plastic pots with the diameter of 25 cm, containing peat-vermiculite mixture (1:1). The plants were later thinned out to 20 wheat plants per pot.

The pots were top-watered twice a week (pF value 2.0) until the plants had developed to the three-leaf stage. The pots were then divided into two groups, one of which (10 pots) was maintained at pF 2.0 and the other (10 pots) was subjected to moderate water stress (pF 3.0). At the four-leaf stage the plants were sprayed with 25 ml of solution containing 0.1% of the adjuvant LI-700 (Loveland Industries Inc., Greeley, Colo., USA) and different concentrations of betaine (Cultor Oy, Finnsugar Bioproducts) as follows: 0M (control), 0.015M, 0.05M, 0.1M and 0.3M betaine.

The betaine content of the plants was measured in the following manner. A whole plant was picked from each pot 2, 4, 7, 14 and 21 days after the spraying, washed under running water, dried on a paper towel and submerged into liquid nitrogen, followed by pulverization in a mortar. The powder was put into a cryotube (volume 3.6 ml, Nunc) and the tubes were stored in liquid nitrogen until they were analyzed with HPLC [Rajakylä and Paloposki, *J. Chromatography* 282 (1983) 595–602].

The dry matter content of the plants was measured by picking a whole plant from each pot also 2, 4, 7, 14 and 21 days after the spraying. The plant was weighed, dried at 100° C. overnight and weighed again.

The statistical analyses of results from several greenhouse experiments were performed as factorial analysis with the MSTAT program.

The results of the experiments are shown in Table 5. The results showed no significant differences in the betaine absorption of wheat under stress conditions and under normal conditions, i.e. a stress situation did not considerably affect the betaine absorption. On the other hand, the betaine concentration of the exogenously applied solution had a significant effect on the amount of betaine that was accumulated. The betaine content of plants decreased considerably from the first sampling to the last, which probably resulted from the increased biomass of the plants. On the basis of the results, a betaine content of 0.1M to 0.3M is considered preferable.

TABLE 5

Betaine content of wheat after treatment (I = 2 days, II = 4 days, III = 7 days, IV = 14 days, V = 21 days after treatment, optimum pF2, stress pF3)

| betaine concentration (M) of the solution used | optimum bet. % | stress bet. % | optimum μmol/g dm | stress μmol/g dm |
|---|---|---|---|---|
| 0M, I | 0.54 | 0.57 | 46.06 | 48.94 |
| 0M, II | 0.28 | 0.45 | 23.78 | 38.21 |
| 0M, III | 0.25 | 0.47 | 21.61 | 39.98 |
| 0M, IV | 0.25 | 0.22 | 21.11 | 18.78 |
| 0M, V | 0.18 | 0.42 | 15.61 | 36.11 |
| 0.015M, I | 0.48 | 0.61 | 40.81 | 51.85 |
| 0.015M, II | 0.37 | 0.54 | 31.32 | 46.01 |
| 0.015M, III | 0.34 | 0.52 | 29.27 | 43.99 |
| 0.015M, IV | 0.31 | 0.43 | 26.73 | 36.86 |
| 0.015M, V | 0.19 | 0.28 | 16.31 | 24.14 |
| 0.05M, I | 0.74 | 0.89 | 63.37 | 76.19 |
| 0.05M, II | 0.51 | 0.47 | 43.90 | 39.74 |
| 0.05M, III | 0.41 | 0.58 | 34.58 | 49.33 |
| 0.05M, IV | 0.23 | 0.37 | 19.53 | 31.96 |
| 0.05M, V | 0.17 | 0.34 | 14.52 | 29.23 |
| 0.1M, I | 1.32 | 0.84 | 112.34 | 71.71 |
| 0.1M, II | 0.79 | 1.06 | 67.44 | 90.89 |
| 0.1M, III | 0.73 | 0.56 | 62.36 | 47.82 |
| 0.1M, IV | 0.48 | 0.42 | 40.70 | 36.15 |
| 0.1M, V | 0.31 | 0.38 | 26.17 | 32.05 |
| 0.3M, I | 2.86 | 2.77 | 244.25 | 236.22 |
| 0.3M, II | 1.93 | 1.93 | 164.53 | 164.75 |
| 0.3M, III | 0.92 | 1.47 | 78.19 | 125.63 |
| 0.3M, IV | 0.67 | 1.03 | 56.95 | 88.10 |
| 0.3M, V | 0.53 | 0.73 | 45.55 | 61.95 |

EXAMPLE 6

The experiments were conducted in the manner of Example 5, except that the plants were sprayed before flowering and only the leaves were used for the analysis.

The betaine content and dry matter content of the leaves were determined in the manner described in Example 5.

The statistical analyses of results from several greenhouse experiments were performed as factorial analysis with the MSTAT program.

This experiment showed considerable interaction between the stress treatment and the betaine concentration used. The betaine concentration used also had a significant effect on the amount of accumulated betaine. The results are shown in Table 6.

TABLE 6

Betaine content of wheat after treatment (I = 2 days, II = 4 days, III = 7 days, IV = 14 days, optimum pF2, stress pF3)

| betaine concentration (M) of the solution used | optimum bet. % | stress bet. % | optimum μmol/g dm | stress μmol/g dm |
|---|---|---|---|---|
| 0M, I | 0.022 | 0.023 | 1.898 | 1.924 |
| 0M, II | 0.010 | 0.038 | 0.858 | 3.250 |
| 0M, III | 0.017 | 0.021 | 1.459 | 1.797 |
| 0M, IV | 0.026 | 0.021 | 2.208 | 1.820 |
| 0.015M, I | 0.013 | 0.033 | 1.132 | 2.824 |
| 0.015M, II | 0.018 | 0.033 | 1.579 | 2.831 |
| 0.015M, III | 0.033 | 0.029 | 2.813 | 2.446 |
| 0.015M, IV | 0.034 | 0.036 | 2.932 | 3.084 |
| 0.05M, I | 0.042 | 0.022 | 3.565 | 1.869 |
| 0.05M, II | 0.052 | 0.040 | 4.433 | 3.428 |
| 0.05M, III | 0.065 | 0.029 | 5.568 | 2.483 |
| 0.05M, IV | 0.039 | 0.027 | 3.304 | 2.346 |
| 0.1M, I | 0.069 | 0.029 | 5.855 | 2.494 |
| 0.1M, II | 0.058 | 0.112 | 4.954 | 9.539 |
| 0.1M, III | 0.052 | 0.028 | 4.423 | 2.425 |
| 0.1M, IV | 0.031 | 0.018 | 2.618 | 1.570 |
| 0.3M, I | 0.117 | 0.089 | 10.004 | 7.622 |
| 0.3M, II | 0.133 | 0.059 | 11.339 | 5.043 |
| 0.3M, III | 0.116 | 0.065 | 9.335 | 5.561 |
| 0.3M, IV | 0.101 | 0.029 | 8.658 | 2.495 |

EXAMPLE 7

This experiment examined the effect of different adjuvants on betaine absorption. The experiments were conducted in the manner of Example 5 utilizing wheat plants but without subjecting them to water stress. Pots containing wheat plants were sprayed at the four-leaf stage of the plants with 25 ml of 0.1M betaine solution containing 0.1% of different adjuvants as follows: control with no adjuvant, LI-700 (Loveland Industries Inc.), Agrirob (Robbe SA., France), Activator (Loveland Industries Inc.). The other control consisted of pots containing untreated wheat plants. Dry matter and betaine samples were gathered, as described in Example 5, 2 and 10 days after the spraying, and the betaine and dry matter contents of the plants were determined in the manner of Example 5.

The statistical analyses of results from several greenhouse experiments were performed as factorial analysis with the MSTAT program.

The adjuvants clearly improved betaine absorption. When no adjuvant was used, betaine absorption was about 5%, whereas the use of adjuvant increased the absorption even up to 19%. The best results for wheat were obtained with the adjuvant LI-700 (19%), and the second best was Activator (13%). The betaine absorption percentage with Agrirob was 9%. The results are shown in Table 7.

TABLE 7

Effect of adjuvant on the betaine content of wheat

| Treatment | Betaine content of wheat (μmol/g dm) |
|---|---|
| Control (water) | 32.84 |
| Control (water + betaine) | 58.05 |
| LI-700 | 129.57 |
| Activator | 123.30 |
| Agrirob | 82.27 |

EXAMPLE 8

This experiment examined the effect of different adjuvant concentrations on betaine absorption. Fifty wheat seeds were sown in each 7.5 litre pot, and the seeds were later thinned to 40 wheat plants per pot. The pots were watered twice a week to a pF value of 2.0. At the three-leaf stage of the plants, half of the pots were stressed to pF 3. At the four-leaf stage the plants were treated with 15 ml of 0.1M betaine solution containing adjuvant as follows: 0.05% LI-700, 0.5% LI-700 (Loveland Industries Inc.), 0.1% Sito+ (Witco As), 0.5% Sunoco (Sun Oil Company), 0.15% Agrirob (Robbe SA., France), or containing no adjuvant. Pots containing wheat plants that were not treated at all were used as control. One plant from each pot was picked for betaine analysis and one plant for dry matter determination 1, 6 and 24 hours after the solution was applied. The betaine and dry matter contents of the plants were determined in the manner described in Example 5.

The statistical analyses of results from several greenhouse experiments were conducted as factorial analysis with the MSTAT program.

The results show that both the adjuvant used and the absorption time affected the betaine absorption. Interaction was also detected between the absorption time and the treatment and between the adjuvant and the absorption time. The best results for wheat were obtained with the adjuvant Sito+ under stress conditions and the adjuvant LI-700 (0.5%) under optimum conditions. Numerical results are shown in Table 8.

TABLE 8

Effect of adjuvant on the betaine content of wheat

| Treatment | Conditions | Wheat betaine content after treatment ($\mu$mol/g dm) | | |
|---|---|---|---|---|
| | | 1 h | 6 h | 24 h |
| control, water | optimum | 37.29 | 35.17 | 41.61 |
| control, water + betaine | optimum | 52.95 | 45.65 | 98.26 |
| Sito+ | optimum | 84.87 | 104.62 | 80.44 |
| Sunoco | optimum | 49.16 | 51.18 | 52.10 |
| Agrirob | optimum | 60.87 | 42.97 | 48.45 |
| LI-700, 0.05% | optimum | 48.79 | 66.34 | 50.19 |
| LI-700, 0.5% | optimum | 88.47 | 107.17 | 78.50 |
| control, water | stress | 65.61 | 68.48 | 55.01 |
| control, | stress | 64.54 | 60.72 | 114.88 |

TABLE 8-continued

Effect of adjuvant on the betaine content of wheat

| Treatment | Conditions | Wheat betaine content after treatment ($\mu$mol/g dm) | | |
|---|---|---|---|---|
| | | 1 h | 6 h | 24 h |
| water + betaine | | | | |
| Sito+ | stress | 108.94 | 99.43 | 122.64 |
| Sunoco | stress | 78.35 | 72.74 | 86.79 |
| Agrirob | stress | 83.52 | 76.78 | 86.78 |
| LI-700, 0.05% | stress | 63.81 | 70.05 | 56.22 |
| LI-700, 0.5% | stress | 68.02 | 122.84 | 140.83 |

We claim:

1. A method for synergistically improving the yield of plants growing under stress conditions, said method comprising exogenously applying to a viable plant of an enhanced combination of glycinebetaine, applied at a rate of about 1 to about 30 kg/ha and at least one adjuvant to improve glycinebetaine absorption of plant cells, wherein the adjuvant is selected from the group consisting of an agent affecting glycinebetaine absorption, a surfactant, a fixing agent, a wetting agent and a phospholipid activating agent.

2. A method according to claim 1, wherein glycinebetaine and adjuvant are applied separately or simultaneously.

3. A method according to claim 1, wherein glycinebetaine is used in an amount of about 2 to 30 kg/ha, and adjuvant about 0.05 to 5.0 l/ha.

4. A method according to claim 1, wherein an aqueous solution containing 0.01M to 0.5M glycinebetaine and 0.01 to 1.0% of adjuvant is used.

5. A method according to claim 4, wherein the adjuvant is a lecithin-based activating additive or a fixing agent containing ethoxylated alcohol.

6. A method according to claim 3, wherein glycinebetaine is used in an amount of about 2 to 4 kg/ha and adjuvant about 0.05 to 5.0 l/ha.

* * * * *